US012626494B2

(12) United States Patent
Ali et al.

(10) Patent No.: US 12,626,494 B2
(45) Date of Patent: May 12, 2026

(54) ULTRASOUND IMAGE FEATURE SEGMENTATION

(71) Applicants:GE Precision Healthcare LLC, Wauwatosa, WI (US); The General Hospital Corporation, Boston, MA (US)

(72) Inventors: Abder-Rahman Ali, Halifax (CA); Michael Wang, Wauwatosa, WI (US); Michael J. Washburn, Brookfield, WI (US); Yelena Tsymbalenko, Mequon, WI (US); Anthony E. Samir, Newton, MA (US); Viksit Kumar, Quincy, MA (US); Shuhang Wang, Newton, MA (US); Theodore Pierce, Auburndale, MA (US); Qian Li, Boston, MA (US); Arinc Ozturk, Boston, MA (US)

(73) Assignees: GE Precision Healthcare LLC; The General Hospital Corporation

( * ) Notice: Subject to any disclaimer, the term of this patent is extended or adjusted under 35 U.S.C. 154(b) by 95 days.

(21) Appl. No.: 18/205,804

(22) Filed: Jun. 5, 2023

(65) Prior Publication Data

US 2024/0404263 A1 Dec. 5, 2024

(51) Int. Cl.
*G06V 10/778* (2022.01)
*A61B 8/00* (2006.01)
*G06T 7/11* (2017.01)

(52) U.S. Cl.
CPC .......... *G06V 10/7792* (2022.01); *A61B 8/485* (2013.01); *G06T 7/11* (2017.01);
(Continued)

(58) Field of Classification Search
CPC ........... G06T 2207/10132; G06T 2207/30056
See application file for complete search history.

(56) References Cited

U.S. PATENT DOCUMENTS

| | | | |
|---|---|---|---|
| 5,810,742 A * | 9/1998 | Pearlman | ........... A61B 17/3403 |
| | | | 600/547 |
| 10,251,627 B2 * | 4/2019 | Parthasarathy | ........ A61B 8/469 |

(Continued)

FOREIGN PATENT DOCUMENTS

WO 2013034878 A3 3/2013

OTHER PUBLICATIONS

Looney [Fully automated, real-time 3D ultrasound segmentation to estimate first trimester placental volume using deep learning, JCI Insight. 2018;3(10):e120178.]. (Year: 2018).*

(Continued)

*Primary Examiner* — Oommen Jacob
(74) *Attorney, Agent, or Firm* — MCANDREWS HELD & MALLOY, LTD; Daniel Bissing; David Bates

(57) ABSTRACT

By example, a method for training a model to segment test images, wherein the test images comprise ultrasound image data, includes: receiving, at a self-supervised learning framework, a first plurality of training images, wherein the first plurality of training images include ultrasound data corresponding to patients' livers; processing the first plurality of plurality of training images with a learning algorithm of the self-supervised learning framework, and responsively adapting a trained model; and receiving, at a supervised learning framework, the trained model and a second plurality of training images, wherein the second plurality of training images include ultrasound data corresponding to patients' livers and annotations of the livers, and responsively adapting the trained model.

15 Claims, 3 Drawing Sheets

(52) U.S. Cl.
CPC ............... *G06T 2207/10132* (2013.01); *G06T 2207/20081* (2013.01); *G06T 2207/30056* (2013.01)

(56) References Cited

U.S. PATENT DOCUMENTS

| | | | | |
|---|---|---|---|---|
| 2007/0047786 A1* | 3/2007 | Aklilu | ..................... | G06F 18/28 |
| | | | | 382/128 |
| 2009/0324040 A1* | 12/2009 | Lindop | ............... | G01S 7/52042 |
| | | | | 382/131 |
| 2010/0128946 A1* | 5/2010 | Fidrich | ................... | G06T 7/149 |
| | | | | 382/131 |
| 2011/0046894 A1* | 2/2011 | Stamnes | ............... | A61B 5/7264 |
| | | | | 702/19 |
| 2011/0184292 A1* | 7/2011 | Yoo | ...................... | A61B 8/5269 |
| | | | | 600/447 |
| 2011/0245676 A1* | 10/2011 | Lin | ...................... | G01S 7/52077 |
| | | | | 600/447 |
| 2012/0155734 A1* | 6/2012 | Barratt | ..................... | G06T 7/344 |
| | | | | 382/128 |
| 2014/0171782 A1* | 6/2014 | Bruder | ................. | A61B 5/0035 |
| | | | | 600/411 |
| 2016/0113632 A1* | 4/2016 | Ribes | ..................... | A61B 8/469 |
| | | | | 600/440 |
| 2016/0143621 A1* | 5/2016 | Parthasarathy | ........ | A61B 8/483 |
| | | | | 600/438 |
| 2017/0007098 A1* | 1/2017 | Gora | ..................... | A61B 5/0066 |
| 2018/0108138 A1* | 4/2018 | Kluckner | .................. | G06T 7/11 |
| 2019/0069882 A1* | 3/2019 | Moctezuma de la Barrera | .......... | |
| | | | | A61B 34/10 |
| 2019/0069957 A1* | 3/2019 | Barral | ..................... | A61B 90/37 |
| 2020/0367853 A1* | 11/2020 | Yoo | ......................... | A61B 8/085 |
| 2021/0056684 A1* | 2/2021 | Zhou | ....................... | G06V 10/82 |
| 2021/0128114 A1* | 5/2021 | Patil | ......................... | A61B 8/54 |
| 2021/0177373 A1* | 6/2021 | Xie | ......................... | A61B 8/463 |
| 2022/0101518 A1* | 3/2022 | Tsymbalenko | ......... | G16H 50/30 |
| 2022/0223293 A1* | 7/2022 | Steinberg-Koch | ....... | G06N 3/09 |
| 2022/0237798 A1* | 7/2022 | Kumar | .................. | G06T 7/0012 |
| 2022/0249061 A1 | 8/2022 | Carrascal et al. | | |
| 2022/0262105 A1* | 8/2022 | Zhou | ....................... | G06N 3/088 |
| 2024/0404263 A1* | 12/2024 | Ali | ............................ | G06T 7/11 |

OTHER PUBLICATIONS

Chen, T., Kornbligh S., Norouzi M., Hinton, G., 2020. A simple framework for contrastive learning of visual representations. Proceedings of the 37th International Conference on Machine Learning, PMLR119:1597:1607.

Paszke, A., Chaurasia, A., Kim, S., Culurciello, E., 2016. ENet: A deep neural network architecture for real-time semantic segmentation. In: arXiv preprint arXiv: 1606:02147.

Katramados, I., Breckon, TP. 2011. Real-time visual saliency by division of gaussians. In 18th IEEE International Conference on Image Processing, pp. 1701-1704.

Farraioli, G., et al., 2015. WFUMB guidelines and recommendations for clinical use of ultrasound elastography: Part 3: liver. Ultrasound Med Biol.; 41(5):1161-79.

Redmon, J., Divvala, S., Girshick, R., Farhadi, A., 2016. You only look once: Unfiled, real-time object detection. In Proceedings of the IEEE conference on computer vision and pattern recognition 2016. pp. 779-778.

Ronneberger, O, Fischer, P, Brox, T. U-net: Convolutional networks for biomedical image segmentation. In Medical Image Computing and Computer-Assisted Intervention—MICCAI 2015: 18th International Conference, Munich, Germany, Oct. 5-9, 2015, Proceedings, Part III 18 2015 (pp. 234-241). Springer International Publishing.

* cited by examiner

ULTRASOUND IMAGE FEATURE SEGMENTATION

CROSS REFERENCE TO RELATED APPLICATIONS

[Not Applicable]

BACKGROUND

Generally, this application relates to ultrasound imaging and shear wave elastography. Non-alcoholic fatty liver disease (NAFLD), a cause of chronic liver disease, can be characterized or caused by the accumulation of excess fat in the liver, leading to damage and inflammation. Currently, there is upward trend in the incidence of NAFLD in the U.S., resulting in substantial medical costs. Liver biopsy can be used to diagnose NAFLD but it is invasive, relatively expensive, and may be subject to sampling error and interpretative variability. Due to these limitations, non-invasive alternatives have been developed, including ultrasound. As NAFLD progresses, liver stiffness increases, making it a biomarker. Shear wave elastography (SWE) is an ultrasound method, which can measure or estimate stiffness of liver tissue.

SUMMARY

According to embodiments, a method for training a model to segment test images, wherein the test images comprise ultrasound image data, includes: receiving, at a self-supervised learning framework, a first plurality of training images, wherein the first plurality of training images include ultrasound data corresponding to patients' livers; processing the first plurality of plurality of training images with a learning algorithm of the self-supervised learning framework, and responsively adapting a trained model; and receiving, at a supervised learning framework, the trained model and a second plurality of training images, wherein the second plurality of training images include ultrasound data corresponding to patients' livers and annotations of the livers, and responsively adapting the trained model. The self-supervised learning framework may include a contrastive learning framework. The self-supervised learning framework may employ a convolutional neural network as an encoder. The self-supervised learning framework may employ a projection head. The self-supervised learning framework may include a SimCLR framework. The supervised learning framework may include an ENet framework. The self-supervised learning framework may include a SimCLR framework and the supervised learning framework comprises an ENet framework. The supervised learning framework may include an encoder including a plurality of stages and a decoder including a plurality of stages, wherein each stage includes a plurality of bottleneck modules configured to manage dimensionality. The supervised learning framework may include a maximum pooling layer, wherein the supervised framework further comprises a decoder including a maximum unpooling layer and a spatial convolution algorithm. The supervised learning framework may be configured to avoid bias terms in projections.

According to embodiments, a method for segmenting structures in ultrasound image data includes: obtaining, using ultrasonic energy, ultrasound image data of a patient, including a liver; receiving, at a processor, the ultrasound image data; executing, by the processor, inference instructions to segment, in the ultrasound image data, the liver in real-time to form a segmented liver; and presenting, on a display, the ultrasound image data. The method may further include: determining a region of interest within the segmented liver; and performing shear-wave elastography on data obtained from the region of interest. The region of interest may be automatically determined. The method may further include executing, by the processor, inference instructions to segment, in the ultrasound image data, a poor-probe-contact region. The method may further include presenting, on the display, information corresponding to the poor-probe-contact region with the ultrasound image data.

According to embodiments, a system includes: an ultrasound probe and receiver configured to obtain ultrasound image data of a patient, including a liver; a processor configured to receive the ultrasound image data and to execute inference instructions to segment, in the ultrasound image data, the liver in real-time to form a segmented liver; and a display configured to present the ultrasound image data and information associated with the segmented liver. The processor may be further configured to determine a region of interest within the segmented liver, and cause a shear-wave elastography process to be performed to obtain shear-wave elastography data from the region of interest. The region of interest may be automatically determined. The processor may be further configured to execute inference instructions to segment, in the ultrasound image data, a poor-probe-contact region. The display may be further configured to present information corresponding to the poor-probe-contact region with the ultrasound image data.

Figure 1:
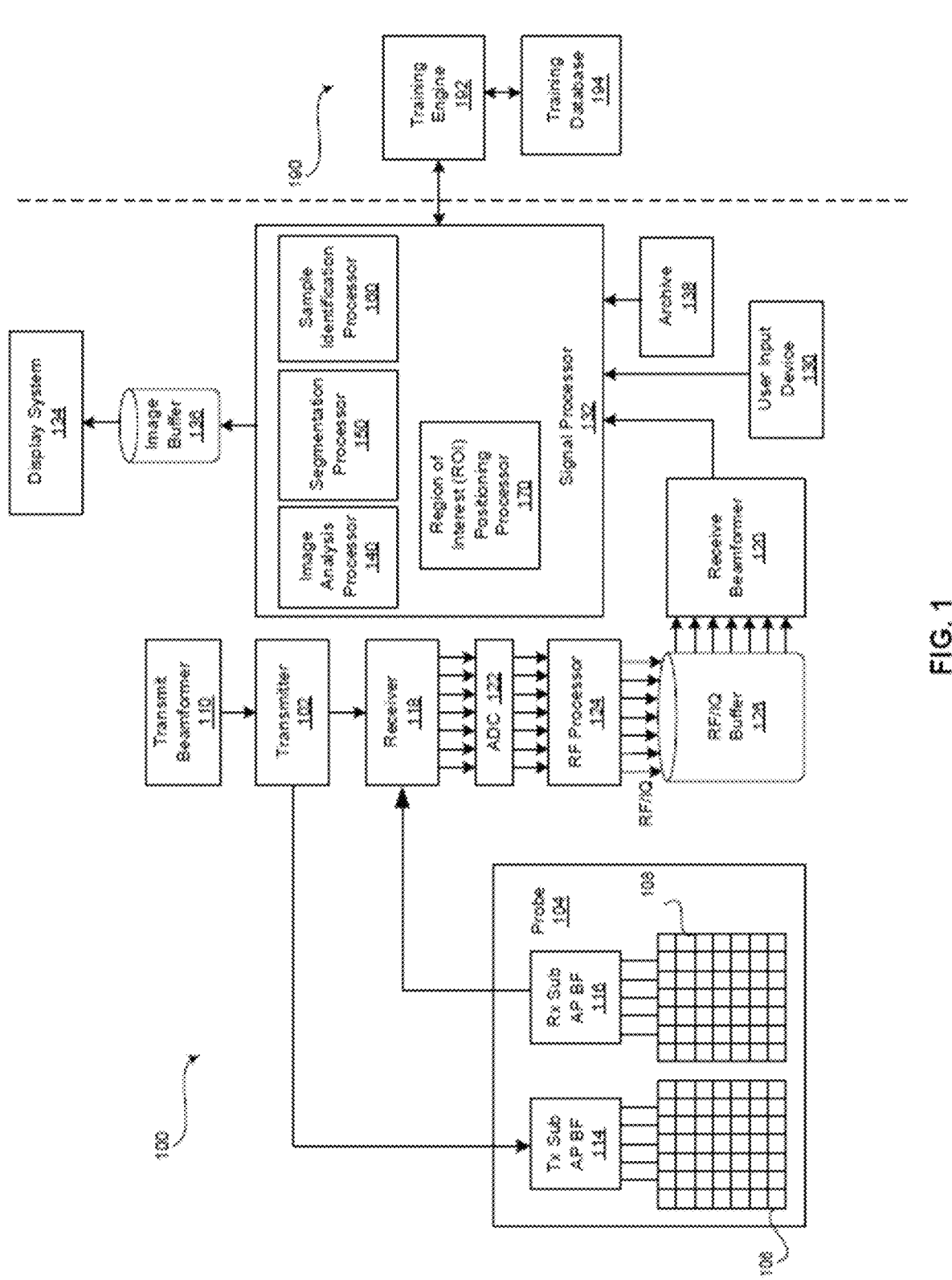
FIG. 1 illustrates an ultrasound system, according to embodiments.

The foregoing summary, as well as the following detailed description of certain techniques of the present application, will be better understood when read in conjunction with the appended drawings. For the purposes of illustration, certain techniques are shown in the drawings. It should be understood, however, that the claims are not limited to the arrangements and instrumentality shown in the attached drawings.

DETAILED DESCRIPTION

Disclosed herein are embodiments for training and using a model using machine learning for segmenting ultrasound image data of a patient. One example of segmentation is for a liver capsule and/or liver (herein, "liver" unless specified otherwise). Another example of segmentation is for image data obtained based on poor probe contact. A segmented organ (e.g., the liver) may be used for locating one or more regions of interest (herein, "region of interest" or "ROI" unless specified otherwise). This ROI may be a location from where shear-wave elastography data is obtained. The shear-wave elastography measurements may indicate a stiffness of the patient's liver, and may be useful for diagnosing NAFLD. The region of interest may be automatically located or location may be facilitated through an automatic process. Embodiments of such processes are disclosed in U.S. Ser. No. 18/205,809, filed on Jun. 5, 2023, the entirety of which is incorporated by reference herein.

Disclosed herein are embodiments of ensemble machine learning processes that reduce the need for a relatively large annotated dataset for training. Instead, relatively smaller annotated datasets may be used. For example, in order to train a model to segment livers in ultrasound image data, annotated images may be provided to the learning framework, where the annotations include the shapes of the livers. Creating these annotations may require manual steps, such as a person manually or electronically drawing livers in corresponding images. Such a process of annotation may be relatively time consuming and expensive. Therefore, if fewer annotations are required to train a model, then this may reduce the time and expense of model training.

Embodiments are disclosed for a two-stage learning model, which reduces can reduce a size of annotated training data, which is often used to improve segmentation accuracy in deep learning models. The ensemble includes a first and second framework. The first framework is a contrastive, self-supervised learning framework, in which a model is trained with unannotated ultrasound image data. One example of such a framework is SimCLR. The second framework is a supervised framework, in which the model is further trained with annotated ultrasound image data. An example of such a framework is ENet. The second framework fine tunes the model originally trained by the first framework. The resulting model can be implemented on an ultrasound instrument, along with the second framework, or a variation thereof. Ultrasound image data may be processed with inference instructions in the second framework to segment structures, such as a liver. Multiple regions may be segmented simultaneously, such as a liver and a poor probe contact region. The segments can be used to determine a region of interest, which can indicate a location in the liver from which to track the propagation of shear waves as part of a shear-wave elastography process. Embodiments of such an ensemble learning model are described in Liver Segmentation in Ultrasound Images Using Self-Supervised Learning with Physics-inspired Augmentation and Global-Local Refinement, 36th Canadian Conference on Artificial Intelligence, Jun. 5, 2023, Ali et al, the entirety of which is incorporated by reference herein.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random-access memory, hard disk, or the like) or multiple hardware components. Similarly, the programs may be standalone programs, may be incorporated as subroutines in an operating system, may be functions in an installed software package, or the like. It should be understood that the various embodiments are not necessarily limited to the arrangements and instrumentality shown in the drawings. It should also be understood that embodiments may be combined as would be understood, or that other embodiments may be utilized and that structural, logical and electrical changes may be made without departing from the scope of the various embodiments. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "one embodiment" or "an embodiment" are not intended to be interpreted as excluding the existence of additional embodiments that also incorporate recited features. Moreover, unless explicitly stated to the contrary, embodiments "comprising" or "having" an element or a plurality of elements having a particular property may include additional elements not having that property.

Also as used herein, the term "image" or "image data" broadly refers to both viewable images and data representing a viewable image. Some embodiments generate (or are configured to generate) at least one viewable image. In addition, as used herein, the term "image" or "image data" is used to refer to an ultrasound mode such as B-mode, CF-mode, and/or sub-modes of B-mode and/or CF such as shear-wave elastography imaging (SWEI), TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the calculations for the various embodiments, such as single or multi-core: CPU, Graphics Board, DSP, FPGA, ASIC or a combination thereof.

Various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams." Also, forming of images may be performed using channel combinations that may originate from more than one transmission event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments disclosed herein.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for segmenting a liver in ultrasonic image data.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

FIG. 1 is a block diagram of an exemplary ultrasound system 100 that is operable to segment ultrasound image data and perform further processing on the segmented data, in accordance with various embodiments. Referring to FIG. 1, there is shown an ultrasound system 100 and a training system 190. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as a liver, or any suitable anatomical structure(s), or related features, such as regions where there is poor contact of the ultrasound probe 104 with the patient.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select an examination type, select a desired ultrasound image view, select valid sample identification algorithms, reposition automatically-placed regions of interest, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, a touch pad, a trackball, motion tracking, voice recognition, a mousing device, keyboard, camera and/or any other device capable of receiving a user directive. In certain embodiments, one or more of the user input devices 130 may be integrated into other components, such as the display system 134, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound image data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), an enterprise archive (EA), a vendor-neutral archive (VNA), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise an image analysis processor 140, a segmentation processor 150, a sample identification processor 160, and a region of interest (ROI) positioning processor 170. The signal processor 132 may be capable of receiving input information from a user input device 130 and/or archive 138, receiving image data, generating an output displayable by a display system 134, and manipulating the output in response to input information from a user input device 130, among other things. The signal processor 132, including the image analysis processor 140, the segmentation processor 150, the sample identification processor 160, and the region of interest (ROI) positioning processor 170, may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include an image analysis processor 140 that comprises suitable logic, circuitry, interfaces and/or code that may be operable to analyze acquired ultrasound image data to determine whether a desired ultrasound image view has been obtained. For example, the image analysis processor 140 may analyze ultrasound image data acquired by an ultrasound probe 104 to determine whether a desired view, such any suitable ultrasound image view of the liver, has been obtained. The image analysis processor 140 may direct the signal processor 132 to freeze the view presented at the display system 134 once the desired image view is obtained. The view may be stored at archive 138 and/or any suitable data storage medium. The image analysis processor 140 may include, for example, artificial intelligence image analysis algorithms, one or more deep neural networks (e.g., a convolutional neural network such as ENet) and/or may utilize any suitable image analysis techniques or machine learning processing functionality configured to determine whether a desired view has been obtained. Additionally and/or alternatively, the artificial intelligence image analysis techniques or machine learning processing functionality configured to provide the image analysis techniques may be provided by a different processor or distributed across multiple processors at the ultrasound system 100 and/or a remote processor communicatively coupled to the ultrasound system 100. In various embodiments, the image analysis processor 140 may comprise suitable logic, circuitry, interfaces and/or code that may be operable to provide a quality metric associated with the obtained view. For example, the image analysis processor 140 may analyze the obtained ultrasound image view as a whole, regions of the obtained ultrasound image view, the obtained ultrasound image view segmented by the segmentation processor 150, or the like to provide a quality metric associated with the obtained view. The image analysis processor 140 may be configured to cause the display system 134 to present the quality metric with the obtained ultrasound image view. For example, the quality metric may be a score (e.g., 1, 2, 3, 4, 5), grade (e.g., A, B, C, D, F), rating (e.g., Excellent, Good, Fair, Poor), color-coding (e.g., green, yellow, red), or the like of the obtained ultrasound image view as a whole and/or for each region of the obtained ultrasound image view. The quality metric may assist a user in determining whether to proceed with the obtained view or to acquire additional ultrasound image data. The image analysis processor 140 may store the quality metric at archive and/or any suitable data storage medium.

The signal processor 132 may include a segmentation processor 150 that comprises suitable logic, circuitry, interfaces and/or code that may be operable to segment flow image frames and B-mode frames. The segmentation processor 150 may be used to identify structures or features (e.g., liver or poor probe contact regions) in the obtained ultrasound image data. In this regard, the segmentation processor 150 may include, for example, artificial intelligence image analysis algorithms, one or more deep neural networks (e.g., a convolutional neural network such as ENet) and/or may utilize any suitable form of artificial intelligence image analysis techniques or machine learning processing functionality configured to provide automated segmentation functionality. An example of such image analysis techniques are disclosed in FIG. 3 and corresponding text. For example, segmentation processor may implement framework 370 in association with trained model 360.

Additionally and/or alternatively, the artificial intelligence image analysis techniques or machine learning processing functionality configured to provide the automated segmentation may be provided by a different processor or distributed across multiple processors at the ultrasound system 100 and/or a remote processor communicatively coupled to the ultrasound system 100. For example, the image segmentation functionality may be provided as a deep neural network that may be made up of, for example, an input layer, an output layer, and one or more hidden layers in between the input and output layers. Each of the layers may be made up of a plurality of processing nodes that may be referred to as neurons. For example, the image segmentation functionality may include an input layer having a neuron for each sample or a group of samples from an obtained ultrasound image view of the liver and a kidney. The output layer may have a neuron corresponding to a plurality of pre-defined anatomical structures, such as a liver, a renal cortex, or any suitable anatomical structure. Each neuron of each layer may perform a processing function and pass the processed ultrasound image information to one of a plurality of neurons of a downstream layer for further processing. As an example, neurons of a first layer may learn to recognize edges of structure in the obtained ultrasound image. The neurons of a second layer may learn to recognize shapes based on the detected edges from the first layer. The neurons of a third layer may learn positions of the recognized shapes relative to landmarks in the obtained ultrasound image. The processing performed by the deep neural network may identify anatomical structures or other features and the location of the structures or features in the obtained ultrasound image with a high degree of probability.

In an exemplary embodiment, the segmentation processor 150 may be configured to store the image segmentation information at archive 138 and/or any suitable storage medium. The segmentation processor 150 may be configured to cause the display system 134 to present the image segmentation information with the obtained ultrasound image. The image segmentation information may be provided to the image analysis processor 140 for providing a quality metric associated with the obtained ultrasound image view as discussed above.

Still referring to FIG. 1, the training system 190 may comprise a training engine 192 and a training database 194. The training engine 192 may comprise suitable logic, circuitry, interfaces and/or code that may be operable to train the neurons of the deep neural network(s) (e.g., artificial intelligence model(s)) inferenced (i.e., deployed) by the image analysis processor 140, segmentation processor 150, sample identification processor 160, and/or ROI positioning processor 170. For example, the artificial intelligence model inferenced by the image analysis processor 140 may be trained to automatically identify an ultrasound image view (e.g., a liver capsule or poor-probe-contact regions). The artificial intelligence model inferenced by the segmentation processor 150 may be trained to automatically segment an obtained ultrasound image view to identify anatomies or other ultrasound image data (e.g., a liver or poor-probe-contact regions). As an example, the training engine 192 may train the deep neural networks deployed by the image analysis processor 140 and/or segmentation processor 150 using database(s). The ultrasound images may include ultrasound images of a particular anatomical feature or related structures, such as a liver or region(s) of poor probe contact with the patient's skin, or any suitable ultrasound images and features.

Figure 3:
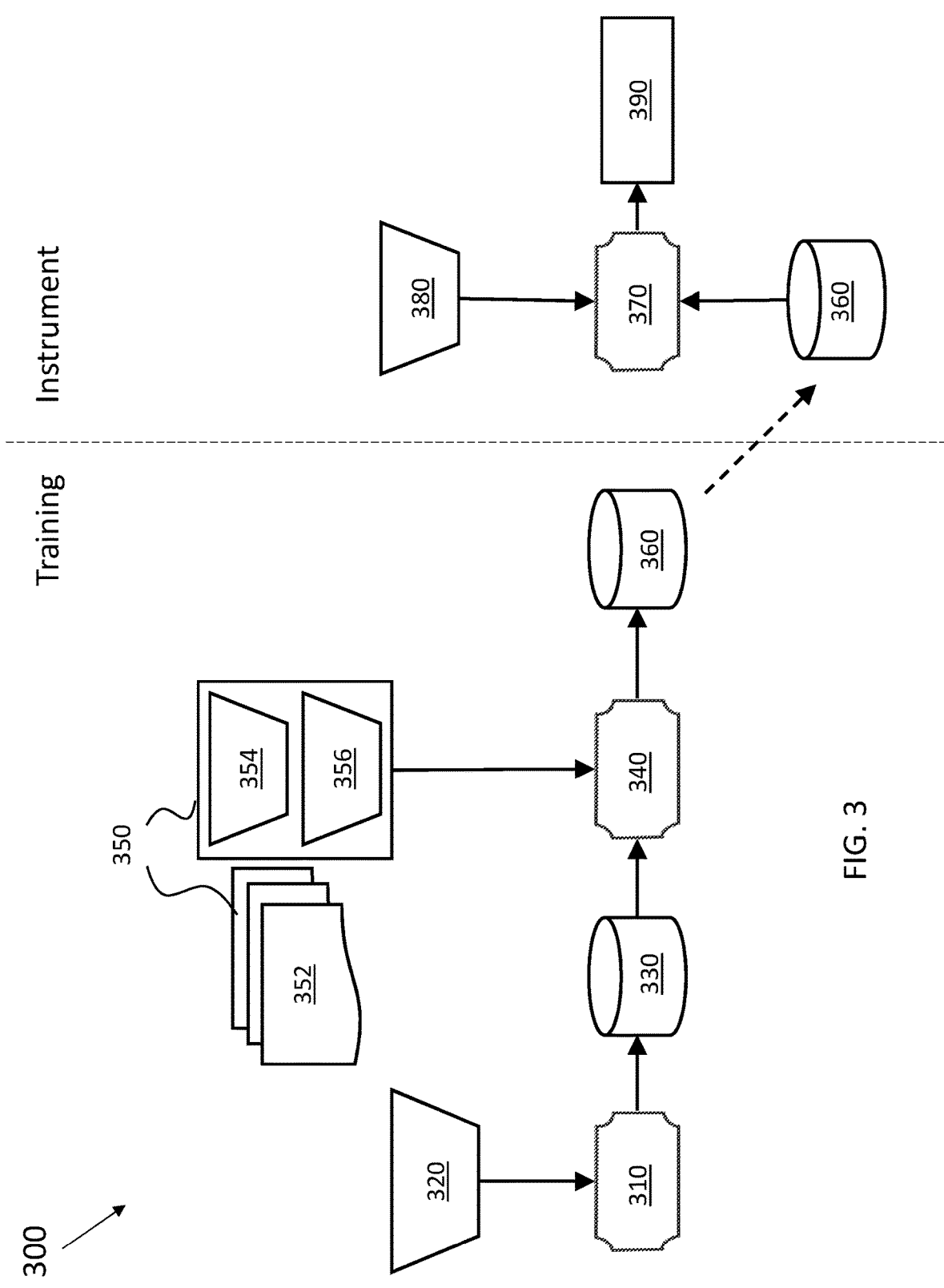
FIG. 3 illustrates a process for training and using a model for segmentation of anatomical image data, according to embodiments.

In certain embodiments, the training system 190 and training database 194 may include components such as those disclosed in FIG. 3 and corresponding text. For example, training engine 192 may include an ensemble framework including a self-supervised learning framework 310 and a supervised learning framework 340. The training database 194 may include datasets, such as dataset 320 for training a model using the self-supervised learning framework 310, and dataset 350 for training a model using the supervised learning framework 340.

In certain embodiments, the training engine 192 and/or training databases 194 may be remote system(s) communicatively coupled via a wired or wireless connection to the ultrasound system 100 as shown in FIG. 1. Additionally and/or alternatively, components or all of the training system 190 may be integrated with the ultrasound system 100 in various forms. In certain embodiments, the training system 190 may be separate from ultrasound system 100, and a model may be trained and then included in ultrasound system 100. For example, a model may be trained to segment a liver capsule or liver and/or poor-probe contact regions, and then the trained model may be included in ultrasound system 100, for example, as part of signal processor 132 or associated memory.

Figure 2:
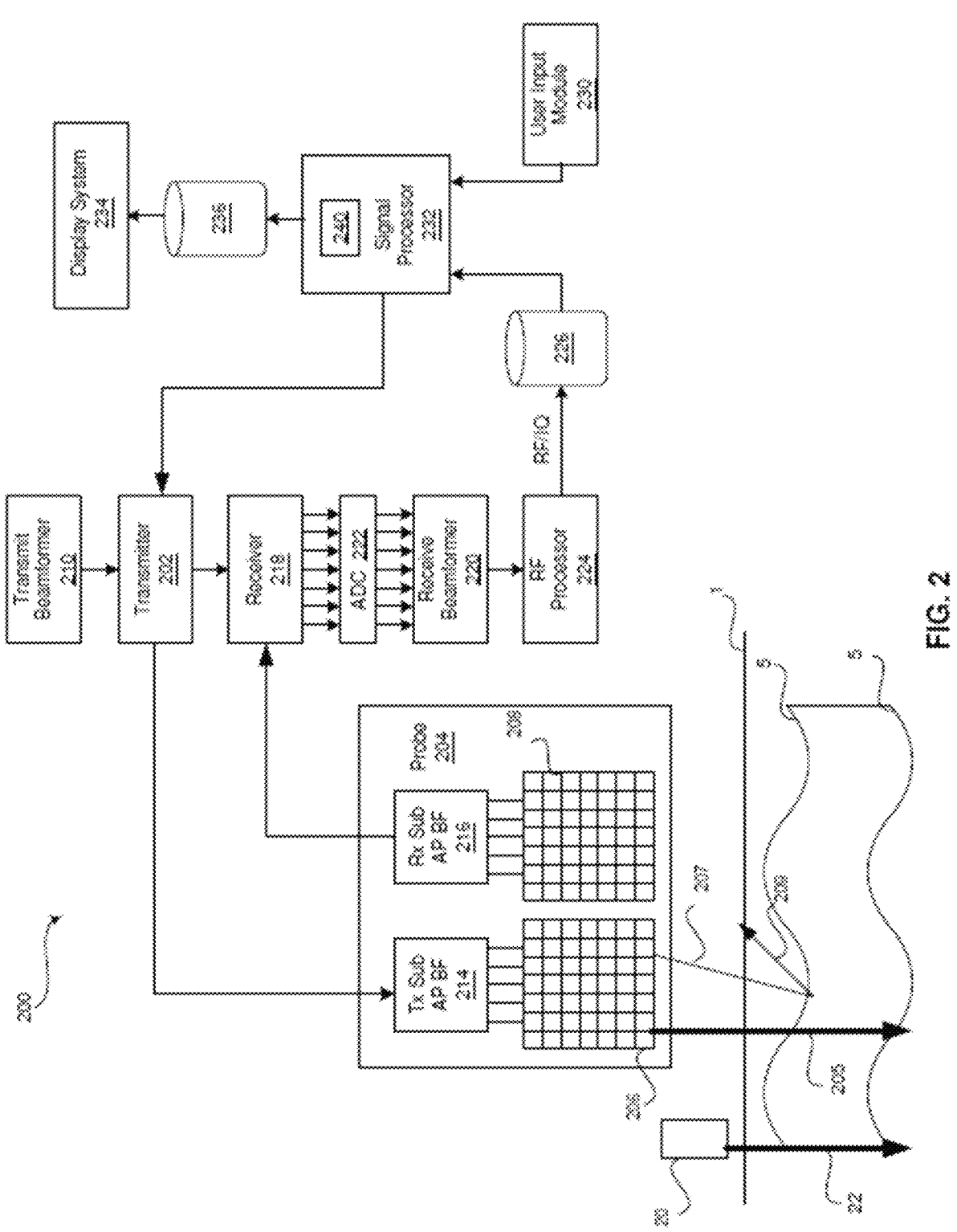
FIG. 2 illustrates an ultrasound system for performing shear-wave elastography, according to embodiments.

FIG. 2 shows a block diagram of an exemplary ultrasound system 200, which is operable to perform a shear-wave elastography process, for example, to obtain information about liver tissue in a region of interest. Ultrasound system 200 may be similar and/or share components with ultrasound system 100. For example, ultrasound system 200 and ultrasound system 100 may be integrated with each other. For example, there may only be one system that performs conventional ultrasound imaging and shear-wave elastography. FIG. 2 illustrates an ultrasound system 200 and a vibration device or transducer 20. The transducer 20 may be external to the ultrasound system 200. The transducer 20 may be configured to provide an external "push" force 22 to create shear waves 5 in a patient's tissue 1. As will be further discussed, the tissue 1 may be liver tissue or tissue or structures proximate to the liver tissue. Additionally and/or alternatively, the ultrasound system 200 itself may provide a push force, such as a relatively high-intensity ultrasonic push pulse 205, for generating the shear waves 5 in the tissue 1. The ultrasound system 200 comprises a transmitter 202 (e.g., similar or the same as transmitter 102), an ultrasound probe (or "probe") 204 (e.g., similar or the same as probe 104), a transmit beamformer 210 (e.g., similar or the same as transmit beamformer 110), a receiver 218 (e.g., similar or the same as receiver 118), a receive beamformer 220 (e.g., similar or the same as receive beamformer 120), an RF processor 224 (e.g., similar or the same as RF processor 124), an RF/IQ buffer 226 (e.g., similar or the same as RF/IQ buffer 126), a user-input module 230 (e.g., similar or the same as user-input module 130), a signal processor 132 (e.g., similar or the same as signal processor 132), an image buffer 236 (e.g., similar or the same as image buffer 136), and a display system 234 (e.g., similar or the same as display system 134.

The transmitter 202 may comprise suitable logic, circuitry, interfaces and/or code that may be operable to drive transducer(s) an ultrasound probe 204. The ultrasound probe 204 may comprise a one dimensional (1D, 1.25D, 1.5D or 1.75D) array or two dimensional (2D) array of transducers, such as piezoelectric elements. The ultrasound probe 204 may comprise transmit transducer elements 106 and receive transducer elements 208, which may be completely coextensive, partially coextensive, or separate.

The transmit beamformer 210 may comprise suitable logic, circuitry, interfaces and/or code that may be operable to control the transmitter 202, which, through a transmit sub-aperture beamformer 214, drives the transmit transducer elements 206 to emit relatively high-intensity ultrasound push pulses 205 into a point of disturbance of the tissue 1 and to emit ultrasonic transmit signals 207 into a region of interest of the tissue 1. As used herein, the term "high-intensity ultrasound push pulses" refers to a derated spatial-peak temporal-average intensity (ISPTA.3) of between 200 and 700 mW/cm$^2$. The transmitted high-intensity ultrasound push pulses 205 may displace the tissue 1 to create shear waves 5 propagating laterally from the point of disturbance. The transmitted ultrasonic signals 207 may be reflected from structures, like the tissue 1 as deformed by the shear waves 5, to produce echoes 209. The echoes 209 are received by the receive transducer elements 208. The group of receive transducer elements 208 in the ultrasound probe 204 may be operable to convert the received echoes 209 into analog signals, undergo sub-aperture beamforming by a receive sub-aperture beamformer 216, and are then communicated to a receiver 218.

The receiver 218 may comprise suitable logic, circuitry, interfaces and/or code that may be operable to receive and demodulate the signals from the receive sub-aperture beamformer 216. The demodulated analog signals may be communicated to one or more of the plurality of A/D converters 222 (e.g., similar to A/D converters 122). The plurality of A/D converters 222 may comprise suitable logic, circuitry, interfaces and/or code that may be operable to convert the demodulated analog signals from the receiver 218 to corresponding digital signals. The plurality of A/D converters 222 are disposed between the receiver 218 and the receive beamformer 220. Notwithstanding, the invention is not limited in this regard. Accordingly, in some embodiments, the plurality of A/D converters 222 may be integrated within the receiver 218.

The receive beamformer 220 may comprise suitable logic, circuitry, interfaces and/or code that may be operable to perform digital beamforming processing on the signals received from the plurality of A/D converters 222. The resulting processed information may be converted back to corresponding RF signals. The corresponding output RF signals that are output from the receive beamformer 220 may be communicated to the RF processor 224. In accordance with some embodiments, the receiver 218, the plurality of A/D converters 222, and the beamformer 220 may be integrated into a single beamformer, which may be digital.

The RF processor 224 may comprise suitable logic, circuitry, interfaces and/or code that may be operable to demodulate the RF signals. In accordance with an embodiment, the RF processor 224 may comprise a complex demodulator (not shown) that is operable to demodulate the RF signals to form I/Q data pairs that are representative of the corresponding echo signals. The RF or I/Q signal data may then be communicated to an RF/IQ buffer 226.

The RF/IQ buffer 226 may comprise suitable logic, circuitry, interfaces and/or code that may be operable to provide temporary storage of the RF or I/Q signal data, which is generated by the RF processor 224.

The user-input module 230 may be utilized to initiate shear-wave elastography imaging, change scan mode, input patient data, surgical instrument data, scan parameters, settings, configuration parameters, and the like. In an exemplary embodiment, the user input module 230 may be operable to configure, manage and/or control operation of one or more components and/or modules in the ultrasound system 200. In this regard, the user-input module 230 may be operable to configure, manage and/or control operation of transmitter 202, the ultrasound probe 204, the transmit beamformer 210, the receiver 218, the receive beamformer 220, the RF processor 224, the RF/IQ buffer 226, the user-input module 230, the signal processor 232, the image buffer 236, and/or the display system 234. The user-input module 230 may be located at various positions on and/or around the ultrasound system 200 such as on the probe 204, at a control panel, and/or at any suitable location.

The signal processor 232 may comprise suitable logic, circuitry, interfaces and/or code that may be operable to process ultrasound information (i.e., RF signal data or IQ data pairs) for presentation on a display system 234. The signal processor 232 is operable to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the RF/IQ buffer 226 during a scanning session and processed in less than real-time in a live or off-line operation. In the exemplary embodiment, the signal processor 232 may comprise a shear wave elastography processing module 240.

The ultrasound system 200 may be operable to continuously acquire ultrasound information at a frame rate that is suitable for the imaging situation in question. Typical frame rates range from 20-70 fps but may be lower or higher. For example, shear-wave elastography imaging may have higher frame rates related to the high pulse-repetition frequency used to image shear waves 5 in tissue 1. In various embodiments, the pulse-repetition frequency in a shear-wave elastography imaging mode is at least 300 pulses/second, and preferably greater or equal to 1000 pulses/second. The acquired ultrasound information may be displayed on the display system 234 at a display-rate that can be the same as the frame rate, or slower or faster. An image buffer 236 is included for storing processed frames of acquired ultrasound information that are not scheduled to be displayed immediately. Preferably, the image buffer 236 is of sufficient capacity to store at least several seconds worth of frames of ultrasound information. The frames of ultrasound information are stored in a manner to facilitate retrieval thereof according to its order or time of acquisition. The image buffer 236 may be embodied as any known data storage medium.

The shear-wave elastography processing module 240 may comprise suitable logic, circuitry, interfaces and/or code that may be operable to handle processing of shear wave ultrasound data to provide information about a region of interest, such as a region of interest in a liver. As used herein, the term "shear-wave ultrasound data" refers to ultrasound information received at the signal processor 232 corresponding with the received echoes 209 produced by the back-scattering of the transmitted ultrasonic signals 207 from structures (e.g., tissue 1) and surgical instruments in the object of interest as deformed by the shear waves 5. In this regard, the shear-wave elastography processing module 240 may comprise suitable logic, circuitry, interfaces and/or code that may be operable to handle processing the shear wave ultrasound data to determine a local distribution of shear wave speed in the tissue 1. The shear-wave speed may be computed by direct inversion of the Helmholtz equation, time-of-flight measurement, or any suitable computational method. The shear-wave ultrasound data may be acquired after a push disturbance is induced in the tissue 1 by the force of a focused ultrasound beam 205 or by an external push force 22, for example. The push disturbance 205, 22 generates shear waves 5 that propagate laterally from the point of disturbance. The ultrasound system 200 acquires the shear-wave ultrasound data using a high pulse repetition frequency. As used herein, the term "high-pulse repetition frequency" refers to a pulse repletion frequency of at least 300 pulses/second. In a preferred embodiment, the pulse repetition frequency used to acquire shear-wave ultrasound data is greater or equal to 1000 pulses/second.

The shear wave elastography processing module 240 may comprise suitable logic, circuitry, interfaces and/or code that may be operable to convert the local distribution of shear wave speed in the tissue 1 to a map, such as a velocity distribution map, an elasticity map, a spatial gradient map, or any suitable map representing the contrast between the needle 10 and surrounding tissue 1. For example, the local distribution may be mapped based on the shear-wave speed to generate a velocity distribution map. As another example, the local distribution may be converted to the elasticity map by computing the stiffness based on Young's modulus, a similar shear modulus, or any suitable conversion computation. Moreover, in various embodiments, a spatial gradient filter may be applied to the velocity distribution map and/or elasticity map to generate a spatial gradient map providing enhanced visualization tissue of interest.

The map represents the speed that the shear wave passed through the tissue at lateral locations from the point of disturbance in the shear-wave ultrasound data. The shear-wave propagation velocity corresponds to the stiffness of the tissue at the lateral locations. Specifically, the higher shear-wave velocity corresponds with more stiffness and the lower shear-wave velocity corresponds with less stiffness. Based on the difference in velocity and/or elasticity of tissue (e.g., region of interest of a liver), the stiffness of the liver can be assessed. For example, the maps may be color-coded or grayscale maps having a range of colors or grays that correspond with the shear-wave speed and/or elasticity. Specifically, an elasticity map may have dark blue or dark gray/black corresponding with soft elasticity to red or light gray/white corresponding with hard elasticity, among other things. The map having the elasticity information may be overlaid on an ultrasound image such as a B-mode image or any suitable ultrasound image.

Additionally and/or alternatively, the shear-wave elastography processing module 240 may comprise suitable logic, circuitry, interfaces and/or code that may be operable to perform image segmentation. In various embodiments, the shear-wave elastography processing module 240 may perform the image segmentation semi-automatically or automatically.

FIG. 3 illustrates a system 300 for training and using a deep learning model in order to segment ultrasound image data. The training portion of system 300 is shown on the left side of the broken line, while the instrument portion of system 300 is shown on the right side. Examples of instruments are described in FIGS. 1 and 2. Training may optionally be performed on, or in conjunction with an instrument. For example, to obtain data for training, ultrasound image data must be obtained, and in some cases, annotated. Training may be performed by one or more processors, hardware, and/or memory, such as those which are discussed herein. One or more machine learning frameworks disclosed herein may be implemented using software for learning frameworks, such as PyTorch or C++. In an embodiment, both the self-supervised learning framework and the supervised learning framework are implemented using the same software. According to such an embodiment, the same model structure may be used for both frameworks.

On the training side of system 300, a self-supervised learning framework 310 and supervised learning framework 340 are provided. Both frameworks 310, 340 include instructions stored in one or more computer readable media, and these instructions are executable by one or more processors. The instructions may be written with source code, such as PyTorch or C++, and then compiled into executable instructions. Framework 310 trains model 330, which is stored in one or more memories. Model 330 is further refined by framework 340, resulting in model 360. Model 360 may be similar to model 330. For example, model 330 and model 360 may have the same structure, but the nodes may have different weighting. Framework 340 refines model 330 with annotated data set 350 to form model 360, which is the model used for segmentation on the instrument.

Framework 310 may receive and process an unannotated data set 320 including ultrasonic image data (e.g., B-mode images). Such images may be referred to as training images. The unannotated data set 320 may include ultrasonic image data from different patients' abdomens, including image data of the patients' livers or regions where there is poor probe contact with the patients. While framework 310 can learn to represent different patterns, appearances, and conditions that appear in liver ultrasound images, it may not inherently understand the real-world meaning of those patterns. To use the learned representations for a specific task (i.e., segmenting the liver or a region of poor-probe contact), framework 340 (discussed below) may be used. Framework 310 can learn high-dimensional representations of images that capture significant visual features but may not be explicitly interpretable in human terms. For liver ultrasound images for instance, framework 310 might learn representations of various textures, patterns, shapes, structures, and contrasts present in the data. Framework 310 may process (e.g., successively process) the images in unannotated data set 320 with a learning algorithm until model 330 is finalized. Framework 310 includes training instructions that are executed by a processor to train model 330 using unannotated data set 320. As framework 310 continues to process training images in unannotated dataset 320, it may correspondingly adapt model 330 in a continuing fashion.

Framework 310 may be a contrastive learning framework for learning of visual representations (e.g., patient livers or poor probe contact regions in the image data). One such framework is SimCLR. Framework 310 may provide for a contrastive loss function, in which a neural network is trained to distinguish between different views of the same image data, rather than, for example, training a model to classify images into a set of predefined categories. Framework 310 may be considered self-supervised as opposed to supervised. Framework 310 trains model 330 without the need for an annotated data set. Framework 310 may include various components. One such component of framework 310 may be stochastic data augmentation—i.e., random cropping followed by resizing back to the original size, random color distortions, and random Gaussian blur augmentation methods may be used (e.g., sequentially) to create two correlated views of the same example (a positive pair). This allows model 330 to learn to distinguish between different views of the same image. Another component of framework 310 may be a feature extractor, such as a convolutional neural network (CNN). Such a CNN may be based on the ResNet-50 architecture. The CNN may map an input image to a feature space and produce a feature representation of the image. Model 330 is then fine-tuned on the target dataset using a contrastive loss function, which is another possible component of framework 310. A contrastive loss function may compare the feature representations of different views of the same image, and attempt to minimize the distance between the representations of the same image while maximizing the distance between the representations of different images. Another component of framework 310 may be a projection head, such as a multilayer perception (MLR) with one hidden layer. The MLR may be used to project a feature representation of the image to a lower-dimensional space, which may be used as a representation of the image that is provided to the contrastive loss function. This may be accomplished by applying a linear transformation followed by a non-linear activation function (such as ReLU) to the feature representation.

In an embodiment for training model 330 with framework 310, during training, a minibatch of N "examples" is randomly selected, and the contrastive prediction task is performed on pairs of augmented examples, resulting in 2N data points. In SimCLR, the term "examples" refers to images that have been altered in certain ways for training purposes. This alteration process, known as data augmentation, can include steps like cropping a portion of the image, changing its colors, or blurring it. These varied versions of the same image are then used by the system to learn how to distinguish between different views of the same image and different images entirely. Instead of explicitly sampling negative examples, all other 2 (N−1) augmented examples within the minibatch are treated as negative examples for a given positive pair. The final loss is computed across all positive pairs within the minibatch, and is defined as:

$$\ell_{i,j} = -\log \frac{\frac{c^{sim}(z_i, z_j)}{\tau}}{\sum_{k=1}^{2N} \mathbb{1}_{[k \ne i]} \frac{c^{sim}(z_i, z_k)}{\tau}}$$

where $\Pi_{[k \ne i]} \in \{0,1\}$ is an indicator function used to determine whether a sample is a positive or negative sample relative to the anchor image (i.e., it evalues to 1 if k is not equal to i). The temperature parameter, $\tau$, controls the degree of similarity between the representations and can be used to regulate the difficulty of the contrastive task (increasing the temperature can result in a softer and less discriminative similarity function, while decreasing the temperature can result in a harder and more discriminative similarity function).

Framework 310 may use relatively large batch sizes (e.g., 256 to 8192 images) and/or may use LARS optimizer. Aggregating the mean and variance of batch normalization over all devices during training may be performed.

After model 330 is trained by framework 310, it is further trained by framework 340, which may be a supervised learning framework. Framework 340 further trains model 330 using dataset 350 to form model 360. Dataset 350 includes training images 354, validation images 356. Training images 354 and validation images 356 are both annotated with annotations 352. Annotations 352 may be of livers and/or regions showing poor probe contact with the patient. Annotations 352 may be manually drawn by clinicians using electronic tools. Different annotations 352 may be associated with each image in dataset 350. Framework 340 may process training images 354 (with annotations 352) first, and then validation images 356 (with annotations 352) in order to train model 360. The validation images 356 may indicate the effectiveness of model 360, while further tuning performance. As framework 340 processes training images 354 and/or validation images 356, framework 340 continues to responsively adapt model 360.

One example of framework 340 is an ENet (Efficient Neural Network) framework. Framework 340 may be a deep neural network architecture for real-time semantic segmentation and may be able to achieve high accuracy in segmenting images while being computationally efficient. Such a framework 340 allows for real-time performance on resource-constrained devices such as medical devices. In the example of ENet, framework 340 architecture is based on ResNet, and is divided into several stages. For example, the first three stages form the encoder part of the network, while the last two stages form the decoder part. Each stage may include several bottleneck modules, which each consist of convolutional layers (e.g., three convolutional layers). These layers can include a 1×1 projection layer to reduce dimensionality, a main convolutional layer, and a 1×1 expansion layer. Batch normalization and PReLU activation may be used between all convolutional layers. In the case of down-sampling, a max pooling layer can be added to the main branch. Framework 340 can use spatial dropout as a regularization technique, with different dropout rates used in different stages. In the decoder, max pooling can be replaced with max unpooling, and padding can be replaced with spatial convolution without bias. The final layer of framework 340 can be a full convolution. Optimizations can be made to framework 340 to improve performance, such as not using or avoiding bias terms in projections to reduce memory usage. Batch normalization may be used between one or more convolutional layers. Furthermore, non-linearity may be used to improve accuracy. The term "non-linearity" in this context refers to activation functions used in the neural network architecture. In a neural network, an activation function may be used to introduce non-linearity into the output of a neuron. This can allow the network to learn from the errors it makes and adjust its weights accordingly, enabling it to model complex, non-linear relationships between its inputs and outputs. In the case of ENet, non-linearity may be introduced through the use of the PReLU activation function.

After model 360 has been trained, it may be used with instruments, such as those disclosed in systems 100, 200 and as discussed above. Framework 370 may be implemented by processor(s), such as segmentation processor 150 or signal processor 232. Framework 370 may intake ultrasound images 380 generated by the instrument, for example, ultrasound image data generated by system 100 or 200. Ultrasound images 380 may be referred to as test images. Framework 370 includes inference instructions, which are used to process ultrasound images 380 using trained model 360. As a result, framework 370 may determine segmentations 390, for example, of livers and/or poor-probe-contact regions in the ultrasound images 380.

Once the segmentations 390 have been determined, they can be used for further processing, for example, by instruments such as those disclosed in systems 100, 200. Examples of further processing are disclosed in embodiments of U.S. Ser. No. 18/205,809, filed on Jun. 5, 2023, the entirety of which is incorporated by reference herein. For example, a segmented liver can be used to automatically determine a location or possible location of a region of interest from which to process data (e.g., data generated by a shear-wave elastography process, such as the ones described in context of FIG. 2). As another example, segmentation of poor-probe-contact region(s) can be used to generate and display indicators to an instrument operator of where the probe has poor contact with the patient's skin. Examples of such a display include display systems 134, 234.

It will be understood by those skilled in the art that various changes may be made and equivalents may be substituted without departing from the scope of the novel techniques disclosed in this application. In addition, many modifications may be made to adapt a particular situation 22 or material to the teachings of the novel techniques without departing from its scope. Therefore, it is intended that the novel techniques not be limited to the particular techniques disclosed, but that they will include all techniques falling within the scope of the appended claims.

The invention claimed is:

1. A method for segmenting structures in ultrasound image data, the method comprising:
obtaining, using ultrasonic energy, ultrasound image data of a patient, including a liver;
receiving, at a processor, the ultrasound image data;
executing, by the processor, inference instructions to inference from a trained artificial intelligence model to segment, in the ultrasound image data, the liver in real-time to form a segmented liver, and to segment a poor-probe-contact region of an ultrasound probe with the patient's skin; and
presenting, on a display, the ultrasound image data and information corresponding to the poor-probe-contact region with the ultrasound image data.

2. The method of claim 1, further comprising:
determining a region of interest within the segmented liver; and
performing shear-wave elastography on data obtained from the region of interest.

3. A system, comprising:
an ultrasound probe and receiver configured to obtain ultrasound image data of a patient, including a liver;
a processor configured to receive the ultrasound image data and to execute inference instructions to inference from a trained artificial intelligence model to segment, in the ultrasound image data, the liver in real-time to form a segmented liver and to segment, in the ultra-sound image data, a poor probe contact region of an ultrasound probe with the patient's skin; and
a display configured to present the ultrasound image data and information associated with the segmented liver and further configured to present information corre-sponding to the poor-probe-contact region with the ultrasound image data.

4. The system of claim 3, wherein the processor is further configured to determine a region of interest within the segmented liver, and cause a shear-wave elastography pro-cess to be performed to obtain shear-wave elastography data from the region of interest.

5. The method of claim 1, wherein the trained artificial intelligence model is adaptively trained by a process com-prising:
receiving, at a self-supervised learning framework, a first plurality of training images, wherein the first plurality of training images include ultrasound data correspond-ing to patients' livers;
processing the first plurality of training images with a learning algorithm of the self-supervised learning framework, and responsively adapting the trained arti-ficial intelligence model; and
receiving, at a supervised learning framework, the trained artificial intelligence model and a second plurality of training images, wherein the second plurality of train-ing images include ultrasound data corresponding to patients' livers and annotations of the patients' livers, and responsively adapting the trained artificial intelli-gence model.

6. The method of claim 5, wherein the self-supervised learning framework comprises a contrastive learning frame-work.

7. The method of claim 6, wherein the self-supervised learning framework employs a convolutional neural network as an encoder.

8. The method of claim 6, wherein the self-supervised learning framework employs a projection head.

9. The method of claim 5, wherein the self-supervised learning framework comprises a SimCLR framework.

10. The method of claim 5, wherein the supervised learning framework comprises an ENet framework.

11. The method of claim 5, wherein the supervised learning framework comprises an encoder including a plu-rality of stages and a decoder including a plurality of stages, wherein each stage includes a plurality of bottleneck mod-ules configured to manage dimensionality.

12. The method of claim 5, wherein the supervised learning framework comprises a maximum pooling layer, wherein the self-supervised framework further comprises a decoder including a maximum unpooling layer and a spatial convolution algorithm.

13. The method of claim 5, wherein the supervised learning framework is configured to avoid bias terms in projections.

14. A system, comprising:
an ultrasound probe and receiver configured to obtain ultrasound image data of a patient, including a liver;
a processor configured to receive the ultrasound image data and to execute inference instructions to inference from a trained artificial intelligence model to segment, in the ultrasound image data, the liver in real-time to form a segmented liver;
a display configured to present the ultrasound image data and information associated with the segmented liver; and
wherein the trained artificial intelligence model is trained by a process comprising:
receiving, at a self-supervised learning framework, a first plurality of training images, wherein the first plurality of training images include ultrasound data correspond-ing to patients' livers;
processing the first plurality of training images with a learning algorithm of the self-supervised learning framework, and responsively adapt the trained artificial intelligence model; and
receiving, at a supervised learning framework, the trained artificial intelligence model and a second plurality of training images, wherein the second plurality of train-ing images include ultrasound data corresponding to patients' livers and annotations of the livers, and adapt adapting the trained artificial intelligence model,
wherein the processor is further configured to execute inference instructions to segment, in the ultrasound image data, a poor-probe-contact region of an ultra-sound probe with a patient's skin, and
wherein the display is further configured to present infor-mation corresponding to the poor-probe-contact region with the ultrasound image data.

15. The system of claim 14, wherein the processor is further configured to determine a region of interest within the segmented liver, and cause a shear-wave elastography process to be performed to obtain shear-wave elastography data from the region of interest.

* * * * *